(12) United States Patent
Inoue et al.

(10) Patent No.: US 9,194,850 B2
(45) Date of Patent: Nov. 24, 2015

(54) MEASUREMENT DEVICE FOR TOTAL ORGANIC CARBON

(75) Inventors: Shinsuke Inoue, Kyoto (JP); Kiyuki Noto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 13/995,292

(22) PCT Filed: Jan. 6, 2011

(86) PCT No.: PCT/JP2011/050099
§ 371 (c)(1),
(2), (4) Date: Aug. 21, 2013

(87) PCT Pub. No.: WO2012/093482
PCT Pub. Date: Jul. 12, 2012

(65) Prior Publication Data
US 2014/0004003 A1    Jan. 2, 2014

(51) Int. Cl.
*G01N 31/12* (2006.01)
*G01N 31/00* (2006.01)
*G01N 33/18* (2006.01)

(52) U.S. Cl.
CPC .............. *G01N 31/12* (2013.01); *G01N 31/005* (2013.01); *G01N 33/1806* (2013.01)

(58) Field of Classification Search
CPC ..................................................... G01N 31/12
USPC ......................................................... 422/83
See application file for complete search history.

(56) References Cited

U.S. PATENT DOCUMENTS

| 5,994,146 A | 11/1999 | Wright et al. |
| 2007/0254374 A1* | 11/2007 | Iharada et al. ............... 436/146 |

FOREIGN PATENT DOCUMENTS

| CN | 2826430 Y | 10/2006 |
| CN | 201307110 Y | 9/2009 |
| CN | 201488944 U | 5/2010 |
| CN | 101907558 A | 12/2010 |
| EP | 1939620 A1 | 7/2008 |
| JP | 06-050956 A | 2/1994 |
| JP | 09-043245 A | 2/1997 |

(Continued)

OTHER PUBLICATIONS

International Search Report dated Feb. 22, 2011, issued in corresponding aplication No. PCT/JP2011/050099.

(Continued)

*Primary Examiner* — Jill Warden
*Assistant Examiner* — Julie Tavares
(74) *Attorney, Agent, or Firm* — Westerman, Hattori, Daniels & Adrian, LLP (57) ABSTRACT

A first flow rate adjustment mechanism (18) and a second flow rate adjustment mechanism (28) are controlled by a flow rate control unit (62) so that a carrier gas flows through a first supply path (56) and a second supply flow rate (57) at a predetermined flow rate. The flow rate control unit (62) includes cell flow rate control means (66) for controlling the first flow rate adjustment mechanism (56) and the second flow rate adjustment mechanism (57) so that the flow rate of the carrier gas introduced into a sample cell (44) in a sparging state, which is a state where the carrier gas is supplied from the first supply path (56) into a syringe pump (4), and the flow rate of the carrier gas introduced into the sample cell (44) in a normal state.

5 Claims, 6 Drawing Sheets

(56) References Cited

FOREIGN PATENT DOCUMENTS

| | | |
|---|---|---|
| JP | 11-326170 A | 11/1999 |
| JP | 2000-121626 A | 4/2000 |
| JP | 2000-155117 A | 6/2000 |
| JP | 2000-298096 A | 10/2000 |
| JP | 2001-318089 A | 11/2001 |
| JP | 2007-093209 A | 4/2007 |
| JP | 2007-163309 A | 6/2007 |
| JP | 4265080 B2 | 5/2009 |
| JP | 2009-294139 A | 12/2009 |
| WO | 93/17333 A2 | 9/1993 |

OTHER PUBLICATIONS

Extended European Search Report dated Aug. 21, 2014, issued in corresponding European Patent Application No. 11854568.0 (6 pages).

Office Action dated Sep. 16, 2014, issued in corresponding Chinese Patent Application No. 2011800690919, with English Translation (14 pages).

* cited by examiner

PRIOR ART

MEASUREMENT DEVICE FOR TOTAL ORGANIC CARBON

TECHNICAL FIELD

The present invention relates to a total organic carbon measuring device (a TOC meter) which converts carbon components in collected sample water into carbon dioxide at an oxidation reaction unit, transfers gas including the carbon dioxide into a sample cell by a carrier gas, and detects the carbon dioxide concentration in the sample gas flowing through the sample cell by a detector.

BACKGROUND ART

Figure 6:
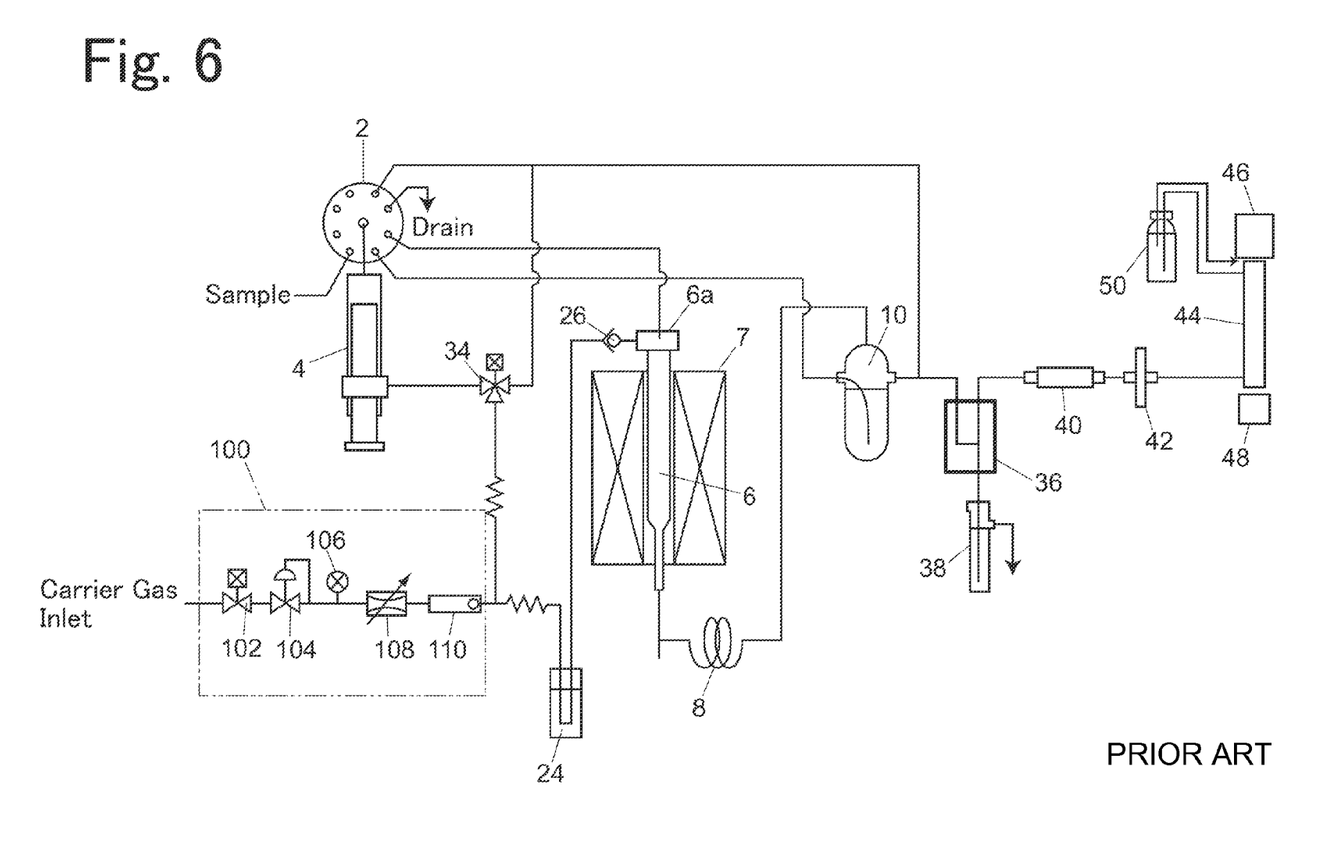
FIG. 6 is a path configuration diagram showing an example of a conventional TOC meter.

A path configuration of a conventional TOC meter is shown in FIG. 6.

A syringe pump 4 is connected to a common port of a multi-port valve 2, and also, a tube for collecting a sample, dilute water or acid, a combustion tube 6, a pure water trap 10 or the like are connected respectively to other ports to be switched and connected to the common port. A path from a carrier gas supply unit 100 is connected to the syringe pump 4 via a three-way electromagnetic valve 34.

Sample water collected by the syringe pump 4 is injected into a sample injection unit 6a at an upper portion of the combustion tube 6 after carbon dioxide gas has been removed inside the syringe pump 4. The sample water injected into the sample injection unit 6a of the combustion tube 6 is supplied from the carrier gas supply unit 100 and guided inside the combustion tube 6 by a humidified carrier gas, and is combusted under the presence of a catalyst inside the combustion tube 6, and carbon components included in the sample water is thereby converted into carbon dioxide.

The gas (carbon dioxide and water vapor) generated in the combustion tube 6 is cooled in a cooling tube 8, and the carbon dioxide is guided into a dehumidification electronic cooler 36 via the pure water trap 10 to have water further removed, has halogen components removed by a halogen scrubber 40, is filtered by a membrane filter 42, and is introduced into a sample cell 44. Then, infrared light from a light source 46 is applied into the sample cell 44, and a signal which is proportional to the carbon dioxide concentration is obtained from a detector 48. Carbon dioxide discharged from the sample cell 44 is adsorbed by a $CO_2$ absorber 50.

The carrier gas supply unit 100 includes, in order from the side of a carrier gas inlet, an electromagnetic valve 102, a pressure adjustment valve 104, a pressure sensor 106, a mass flow controller 108, and a flow meter 110, and is configured in such a way that after a measurer has set, before starting measurement, the pressure and the flow rate of a path through which a carrier gas is to be supplied to be predetermined values, the pressure and the flow rate are maintained to be constant. Carrier gas supply units of conventional TOC meters generally have the same configuration (for example, see Patent Document 1).

The path on the downstream side of the carrier gas supply unit 100 is separated into a path connected to the sample injection unit 6a of the combustion tube 6 and a path connected to the switching valve 34, and the carrier gas flows through both paths at a constant proportion at any time. For example, if the amount of supply is set at 230 mL/min for the carrier gas supply unit 100, the carrier gas flows to the side of the combustion tube 6 at 150 mL/min, and to the side of the switching valve 34 at 80 mL/min. The carrier gas flowing to the side of the switching valve 34 is introduced into the syringe pump 4 by the switching valve 34, or joins the carrier gas that is introduced into the sample cell 44 via the combustion tube 6. The carrier gas which has been introduced into the syringe pump 4 is used as a sparge gas for removing IC (inorganic carbon) in the sample water which has been drawn into the syringe pump 4.

PRIOR ART DOCUMENT

Patent Document

Patent Document 1: Japanese Patent Laid-open Publication No. 2007 93209

SUMMARY OF THE INVENTION

Problems to be Solved by the Invention

As in the example in FIG. 6, conventionally, the flow rate of a carrier gas introduced into the sample cell 44 is different in a state where sparging is performed inside the syringe pump 4 and a state where it is not performed. In the example described above, the flow rate of the carrier gas introduced into the sample cell 44 is 230 mL/min in a normal state and 150 mL/min in a sparging state.

When the flow rate of the carrier gas introduced into the sample cell 44 changes, the level of the baseline of a detection signal obtained by the detector 48 also changes, and when the sparging state is switched to the normal state, the baseline of the detection signal changes. Since measurement of a sample is performed in the normal state, a change in the baseline may seem not to be influential, but in reality, the baseline of the detection signal does not immediately return to the normal state when the sparging state is switched to the normal state, and stabilization at a level in the normal state may take time. If measurement is started before the baseline becomes stable, and a peak appears before the baseline becomes stable, this may result in deterioration in measurement accuracy, for example, by the lead of the peak being distorted and detection of a peak start point becoming difficult. Accordingly, the start of measurement has to be delayed and stabilization of the baseline has to be waited on for to prevent deterioration in the measurement accuracy.

Accordingly, the present invention aims to reduce the time until stabilization of the baseline of a detection signal at a time of switching between a sparging state and a normal state of a syringe pump.

Solutions to the Problems

A TOC meter according to the present invention includes a syringe pump for collecting sample water, an oxidation reaction unit including a combustion tube for oxidatively decomposing, and converting into carbon dioxide, carbon components in the sample water collected by the syringe pump, and a heating furnace for heating the combustion tube, a measurement unit including a sample cell, connected to an outlet portion of the combustion tube, for causing sample gas containing carbon dioxide generated in the combustion tube to flow through, and a detector for measuring carbon dioxide concentration in the sample gas flowing through the sample cell, and a carrier gas supply unit including a carrier gas introduction path for introducing a carrier gas, a first supply path having one end connected to a downstream end of the carrier gas introduction path and other end connected in a manner capable of communicating with the syringe pump, a second supply path, different from the first supply path, having one end connected to the downstream end of the carrier gas introduction path and other end connected to the combustion tube, a first flow rate adjustment mechanism for adjusting a flow rate of the carrier gas flowing through the first supply path, and a second flow rate adjustment mechanism for adjusting, independently from the first flow rate adjustment mechanism, a flow rate of the carrier gas flowing through the second supply path. The first flow rate adjustment mechanism and the second flow rate adjustment mechanism are controlled by a flow rate control unit so that the carrier gas flows through the first supply path and the second supply flow rate at a predetermined flow rate. The flow rate control unit includes cell flow rate control means for controlling the first flow rate adjustment mechanism and the second flow rate adjustment mechanism so that a flow rate of the carrier gas introduced into the sample cell in a sparging state that is a state where the carrier gas is supplied from the first supply path into the syringe pump and a flow rate of the carrier gas introduced into the sample cell in a normal state that is a state where the carrier gas is not supplied from the first supply path into the syringe pump become the same.

According to the TOC meter of the present invention, switching between the sparging state and the normal state may be performed by switching by a path switching mechanism 34A configured to communicate the other end of the first supply path with the syringe pump in the sparging state, and to join the other end to a path between the combustion tube and the sample cell in the normal state. In this case, the flow rate of the carrier gas introduced into the sample cell is, in the normal state, the same as the total flow rate of the carrier gas flowing through both the first supply path and the second supply path, and in the sparging state, the same as the flow rate of the second supply path.

Furthermore, according to the TOC meter of the present invention, the first flow rate adjustment mechanism and the second flow rate adjustment mechanism may adjust the flow rates of carrier gas based on degrees of opening of valves provided on respective paths, the flow rate control unit may hold a first degree of opening that is set in advance as the degree of opening of each valve in the normal state, and a second degree of opening that is set in advance as the degree of opening of each valve in the sparging state, and the cell flow rate control means may be configured to set each valve of the first flow rate adjustment mechanism and the second flow rate adjustment mechanism at the first degree of opening in the normal state and at the second degree of opening in the sparging state. As described above, by setting in advance the degree of opening of each valve of the first flow rate adjustment mechanism and the second flow rate adjustment mechanism for the normal state and for the sparging state, and controlling each valve to be at the corresponding degree of opening according to the state, the configuration of the device may be simplified than a case where the flow rate of the carrier gas flowing through the first supply path, the second supply path or the sample cell is measured and feedback control is performed such that the flow rate is at a predetermined flow rate.

Effects of the Invention

According to the TOC meter of the present invention, the first flow rate adjustment mechanism for adjusting the flow rate of the first supply path and the second flow rate adjustment mechanism for adjusting the flow rate of the second supply path are configured to be capable of performing flow rate adjustment independently of each other, and the flow rate control unit for controlling the adjustment mechanisms includes the cell flow rate control means for controlling the first and second flow rate adjustment mechanisms so that the carrier gas at the same flow rate in both the normal state and the sparging state is introduced into the sample cell, and thus, a change in the baseline of a detection signal at the time of switching from the sparging state to the normal state may be suppressed, and the baseline of the detection signal may be swiftly stabilized. Accordingly, a distortion occurring in the peak shape due to a change in the baseline may be suppressed, and deterioration in the measurement accuracy may be prevented.

EMBODIMENTS OF THE INVENTION

Figure 1:
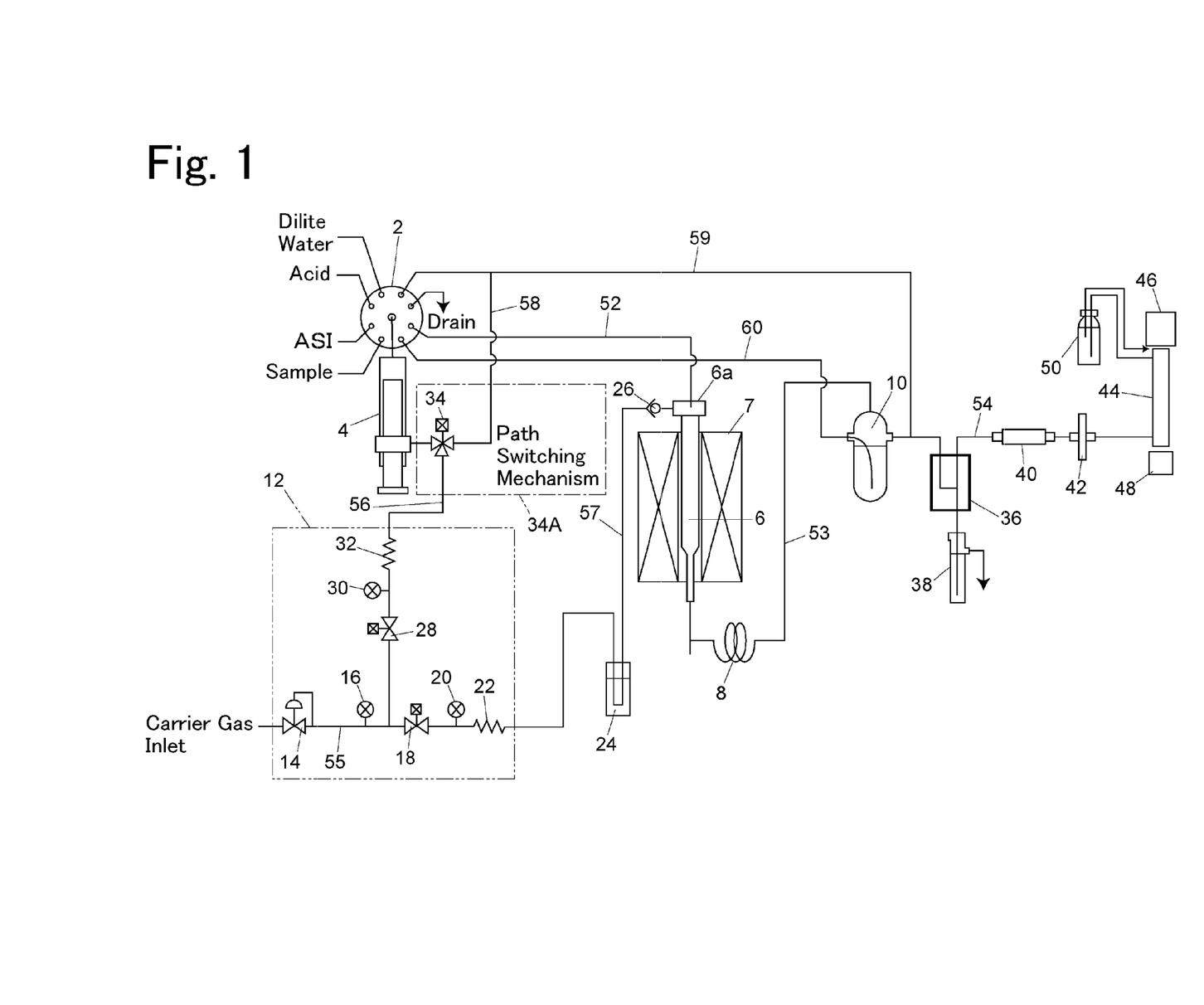
FIG. 1 is a path configuration diagram showing an embodiment of a TOC meter.

Hereinafter, an embodiment of the present invention will be described with reference to FIG. 1.

A TOC meter of this embodiment performs collection by a syringe pump 4, removes inorganic carbon (IC) by sparging in the syringe pump 4, then injects a sample after IC removal into a sample injection unit 6a of a combustion tube 6, introduces the sample into the combustion tube 6 by a carrier gas from a carrier gas supply unit 12, and combusts the sample under the presence of a catalyst housed inside the combustion tube 6 to thereby convert carbon components into carbon dioxide. Sample gas including the carbon dioxide after conversion is further lead to the sample cell 44 by the carrier gas. An infrared ray is applied from a light source 46 on the sample gas which has been introduced into the sample cell 44, carbon dioxide concentration is calculated based on a detection signal obtained at this time by a detector 48, and total organic carbon (TOC) concentration in the sample is obtained based on the carbon dioxide concentration.

The syringe pump 4 is connected to a common port of a multi-port valve 2. In addition to a drain path, a path for collecting a sample (sample water), a path from an autosampler (ASI), a path 52 for injecting sample water to a combustion tube, dilute water and acid, and the like are connected to other ports of the multi-port valve 2.

The syringe pump 4 includes a sparge gas inlet for introducing carrier gas at a lower portion of a barrel. A first supply path 56 from the carrier gas supply unit 12 is connected to the sparge gas inlet of the syringe pump 4 via a three-way electromagnetic valve 34, and carbon dioxide gas (inorganic carbon) in sample water may be removed in the syringe pump 4 using the carrier gas from the carrier gas supply unit 12 as a sparge gas. The three-way electromagnetic valve 34 is capable of switching the connection destination of the first supply path 56 from the carrier gas supply unit 12 between a path joined with the syringe pump 4 and a bypass path 58. The bypass path 58 is connected to a path 59 which is connected to a path 54 joined with the sample cell 44.

One port of the multi-port valve 2 is connected to the sample injection unit 6a provided at an upper portion of the combustion tube 6 via the path 52. The combustion tube 6 includes inside thereof an oxidation catalyst containing metal oxide or a noble metal for converting all the carbon components in a sample into carbon dioxide. An electric furnace 7 is provided around the combustion tube 6, and the temperature inside the combustion tube 6 may be made high (for example, 680° C.). A second supply path 57, which is the other path from the carrier gas supply unit 12, is connected to the sample injection unit 6a of the combustion tube 6 via a check valve 26.

A sample outlet portion provided at a lower portion of the combustion tube 6 is connected to an upper portion of a pure water trap 10 via a cooling tube 8 and a path 53, and the outlet of the pure water trap 10 is connected to the sample cell 44 of a non-disperse infrared (NDIR) method by the path 54. The light source 46 and the detector 48 are arranged facing each other, at both ends of the sample cell 44. The path 54 includes, in order from the upstream side, a dehumidifier 36 for performing dehumidification of a sample, a halogen scrubber 40 for removing halogen components, and a membrane filter 42 for removing foreign matters. A drain pot 38 for removing water is connected to the dehumidifier 36. The bypass path 59 is connected between the pure water trap 10 and the dehumidifier 36 on the path 54.

A carrier gas introduction path 55 of the carrier gas supply unit 12 is separated into the first supply path 56 and the second supply path 57, and is configured to supply a part of the carrier gas introduced from the carrier gas inlet to the side of the first supply path 56, and to supply the rest of the carrier gas to the side of the second supply path 57. A pressure adjustment valve 14 and a pressure sensor 16 are provided on the carrier gas introduction path 55 in the order from the upstream side.

The first supply path 56, which has separated from the carrier gas introduction path 55, includes, from the upstream side, a flow rate control valve 28, a pressure sensor 30 and a path resistor 32 as a first flow rate adjustment mechanism capable of controlling the flow rate by the adjustment of the degree of opening, and the downstream end is connected to one port of the three-way electromagnetic valve 34. The path joined with the syringe pump 4 and the bypass path 58 are connected to other ports of the three-way electromagnetic valve 34, and the first supply path 56 may be connected to either of the paths by the switching by the three-way electromagnetic valve 34.

The second supply path 57, which is the other path which has separated from the carrier gas introduction path 55, includes, from the upstream side, a flow rate control valve 18, a pressure sensor 20, a path resistor 22 and a humidifier 24 as a second flow rate adjustment mechanism capable of controlling the flow rate by the adjustment of the degree of opening, and the downstream end is connected to the sample injection unit 6a of the combustion tube 6 via the check valve 26.

With this TOC meter, measurement of a sample is performed in a state where the first supply path 56 is connected to the bypass path 58 by the three-way electromagnetic valve 34. In the following, this state will be referred to as a "normal state". In this normal state, a carrier gas which has passed through the first supply path 56, the bypass path 58, the path 59 and the path 54, and a carrier gas which has passed through the second supply path 57, the combustion tube 6, the path 53 and the path 54 are introduced into the sample cell 44. That is, in the normal state, a carrier gas is introduced into the sample cell 44 at the total flow rate of the carrier gas which has flowed from the carrier gas supply unit 12 to the side of the first supply path 56 and the carrier gas which has flowed to the side of the second supply path 57. Accordingly, the flow rate of the carrier gas introduced into the sample cell 44 is equal to the flow rate of the carrier gas flowing through the carrier gas introduction path 55.

On the other hand, IC removal by the sparging of sample water drawn into the syringe pump 4 is performed in a state where the first supply path 56 is communicated with the syringe pump 4 by the three-way electromagnetic valve 34. This state is referred to as a "sparging state". In the sparging state, only the carrier gas which has passed through the second supply path 57, the combustion tube 6, the path 53 and the path 54 is introduced into the sample cell 44.

With this TOC meter, the carrier gas supply unit 12 is controlled so that the flow rate of the carrier gas that is introduced into the sample cell 44 is constant at all times. An example of flow rate control will be described assuming that the flow rate of the carrier gas that is introduced into the sample cell 44 is at 230 mL/min. In the normal state, the degrees of opening of the flow rate control valves 18 and 28 are controlled so that the carrier gas flows from the carrier gas supply unit 12 to the side of the first supply path 56 at 80 mL/min, and the carrier gas flows to the side of the second supply path 57 at 150 mL/min.

When the normal state is switched to the sparging state, the carrier gas flowing through the first supply path 56 is introduced into the syringe pump 4 at 80 mL/min as a sparge gas. In the sparging state, a tip end of the syringe pump 4 is connected to the drain by the multi-port valve 2, and the carrier gas leaving the syringe pump 4 is discharged to the drain. At the same time as switching from the normal state to the sparging state, the degree of opening of the flow rate control valve 18 is changed so that the carrier gas flows to the side of the second supply path 57 at 230 mL/min. As described above, since, in the sparging state, only the carrier gas flowing to the side of the second supply path 57 is introduced into the sample cell 44, the flow rate of the carrier gas that is introduced into the sample cell 44 is maintained at 230 mL/min. Additionally, the pressure adjustment valve 14 is controlled based on a measurement value of the pressure sensor 16 in such a way that the pressure inside the carrier gas introduction path 55 is constant at all times.

Figure 2:
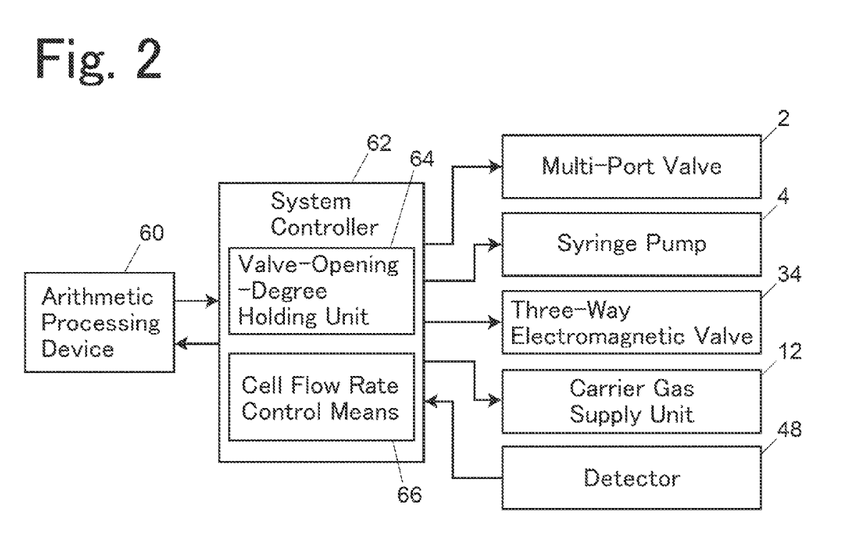
FIG. 2 is a block diagram showing a control system of a carrier gas supply unit of the embodiment.

An example of a control system of the TOC meter is shown in FIG. 2.

Each element of the TOC meter is connected to an arithmetic processing device 60 realized by a personal computer (PC), for example, via a system controller 62. The system controller 62 controls the operation of each element such as the multi-port valve 2, the syringe pump 4, the three-way electromagnetic valve 34 or the carrier gas supply unit 12 according to an instruction from the arithmetic processing device 60. Moreover, the detector 48 is also connected to the arithmetic processing device 60 via the system controller 62, and a detection signal obtained by the detector 48 is transmitted to the arithmetic processing device 60 via the system controller 62, and calculation of a peak area of the detection signal, conversion from a peak area value to a TOC value, and the like are performed by the arithmetic processing device 60.

The system controller 62 includes a valve-opening-degree holding unit 64 and cell flow rate control means 66, and realizes a flow rate control unit. The valve-opening-degree holding unit 64 holds the degrees of opening of the flow rate control valves 18 and 28 in the normal state (the first degrees of opening), and the degrees of opening of the flow rate control valves 18 and 28 in the sparging state (the second degrees of opening). The first degrees of opening of the flow rate control valves 18 and 28 are set so as to cause the flow rate of the carrier gas introduced into the sample cell 44 in the normal state to be a predetermined flow rate. The second degree of opening of the flow rate control valve 28 is set so as to cause the amount of supply of the sparge gas to the syringe pump 4 in the sparging state to be a predetermined flow rate, and the second degree of opening of the flow rate control valve 18 is set so as to cause the flow rate of the carrier gas introduced into the sample cell 44 in the sparging state to be the same as in the normal state.

The cell flow rate control means 66 controls the carrier gas supply unit 12 so that the flow rate of the carrier gas introduced into the sample cell 44 is maintained to be constant at all times. The cell flow rate control means 66 controls the degrees of opening of the flow rate control valves 18 and 28 in the normal state, such as at the time of start of measurement, to be the first degrees of opening, and controls the degrees of opening of the flow rate control valves 18 and 28 in the sparging state where sparging is performed inside the syringe pump 4 to be the second degrees of opening.

Additionally, the degree of opening of the flow rate control valve 28 may also be maintained to be constant. In this case, the amount of supply of sparge gas at the time of performing sparging inside the syringe pump 4 cannot be adjusted, but the flow rate control between the normal state and the sparging state may be performed simply by adjusting the degree of opening of the flow rate control valve 18, and the control system of the carrier gas supply unit 12 may be simplified.

Figure 3:
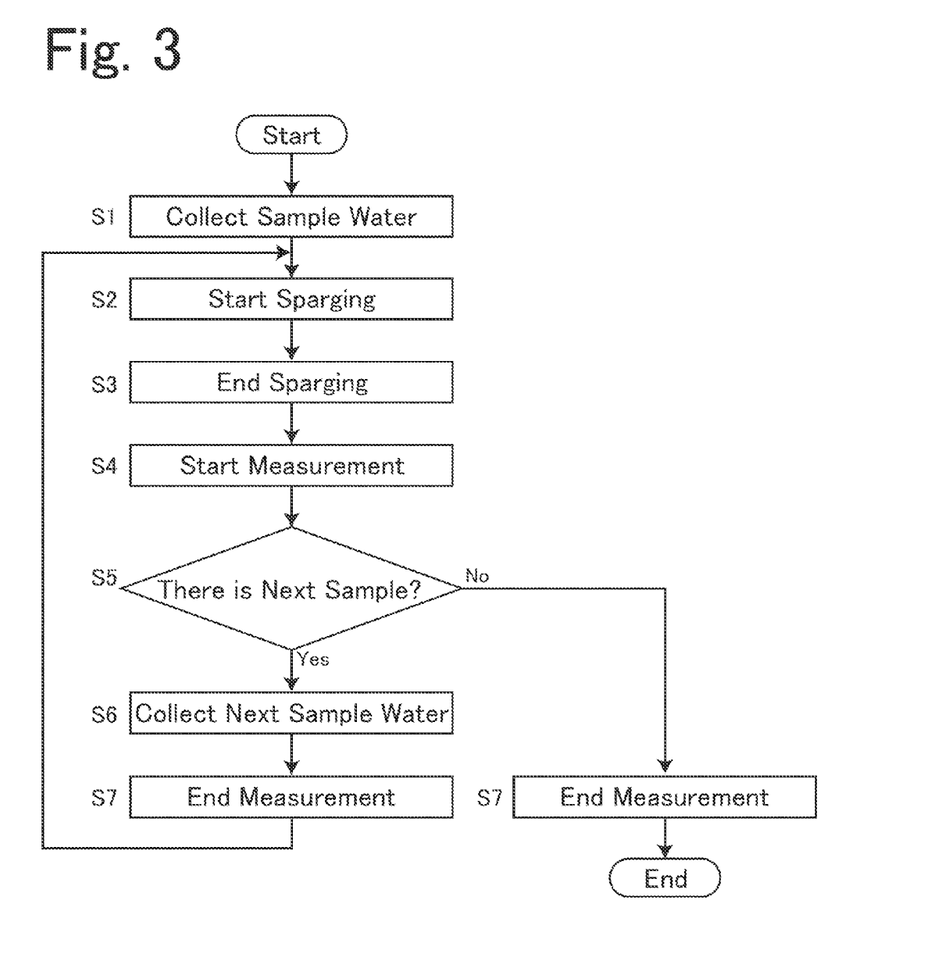
FIG. 3 is a flow chart showing an example of an operation of the embodiment.

An operation of the TOC meter of the embodiment will be described with reference to FIGS. 1 and 3.

In an initial state (=normal state) of this device, the three-way electromagnetic valve 34 connects the first supply path 56 and the bypass path 58, and a carrier gas is introduced into the carrier gas supply unit 12 from the carrier gas inlet at 230 mL/min. The degrees of opening of the flow rate control valves 18 and 28 are each set to the first degree of opening, and a carrier gas flows to the side of the first supply path 56 at 80 mL/min, and to the side of the second supply path 57 at 150 mL/min. A carrier gas is introduced into the sample cell 44 at the total flow rate of 230 mL/min.

First, a predetermined amount of sample water is collected in the syringe pump 4 (step S1). After acid is added to the sample water inside the syringe pump 4, sparging for removing IC in the sample water is started inside the syringe pump 4 (step S2). At the time of starting the sparging, the first supply path 56 is communicated with the inside of the syringe pump 4 by the three-way electromagnetic valve 34 to achieve the sparging state, and at the same time, the degrees of opening of the flow rate control valves 18 and 28 are each set to the second degree of opening. By setting the degree of opening of the flow rate control valve 18 at the second degree of opening, the flow rate of the carrier gas flowing through the second supply path 57 is increased to 230 mL/min, and the flow rate of the carrier gas introduced into the sample cell 44 is maintained at 230 mL/min. When the first degree of opening and the second degree of opening of the flow rate control valve 28 are the same, a sparge gas is supplied to the syringe pump 4 at 80 mL/min. Additionally, by setting the second degree of opening of the flow rate control valve 28 to be greater than the first degree of opening, the flow rate of the sparge gas may be increased and the efficiency of sparging may be increased, enabling the sparging time to be reduced.

At the time of ending the sparging, the first supply path 56 is connected with the bypass path 58 by the three-way electromagnetic valve 34 and the normal state is achieved, and at the same time, the degrees of opening of the flow rate control valves 18 and 28 are each returned to the first degree of opening (step S3). With the path configuration returning to the normal state and the degrees of opening of the flow rate control valves 18 and 28 each returning to the first degree of opening, the flow rate of the carrier gas introduced into the sample cell 44 is maintained at 230 mL/min.

Measurement is started in this state (step S4). The sample water inside the syringe pump 4 is introduced into the sample injection unit 6a of the combustion tube 6. The sample water which has been introduced into the sample injection unit 6a is guided inside the combustion tube 6 by the carrier gas from the second supply path 57 and is combusted under the presence of a catalyst, and all the carbon components are converted into carbon dioxide. Sample gas including the carbon dioxide which has been converted in the combustion tube 6 is guided, together with the carrier gas, to the path 54 via the cooling tube 8, the path 53 and the pure water trap 10.

Here, after deaeration is completed inside the syringe pump 4, the first supply path 56 from the carrier gas supply unit 12 is connected to the bypass path 58, and the carrier gas which has transferred the sample gas from the combustion tube 6 and the carrier gas from the path 59 are joined and made to flow through the path 54.

The sample gas guided to the path 54 is introduced into the sample cell 44 via the dehumidifier 36, the halogen scrubber 40 and the membrane filter 42. Then, infrared light from the light source 46 is applied into the sample cell 44, and a signal according to the concentration of carbon dioxide is obtained by the detector 48. Carbon dioxide discharged from the sample cell 44 is adsorbed by the $CO_2$ absorber 50. The arithmetic processing device 60 calculates the TOC based on the signal obtained by the detector 48, and ends the measurement (step S7).

In the case where there is sample water to be measured next (step S5), the next sample water is drawn into the syringe pump 4 during the measurement described above. The timing of drawing in the next sample water is, for example, immediately after sample water has been introduced from the syringe pump 4 into the combustion tube 6 and the inside of the syringe pump 4 has been cleaned. Then, when the measurement of the first sample is complete, the sparging and the following operation are performed for the next sample. In the case where there is no sample water to be measured next, the operation is ended by the completion of the TOC measurement (step S7).

Figure 4A:
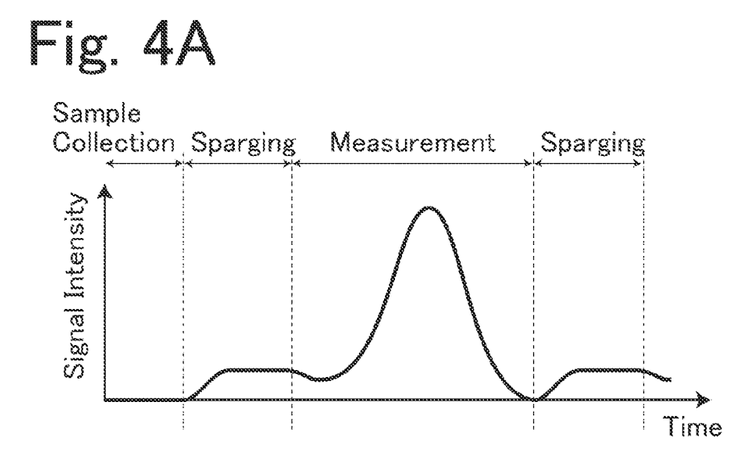
FIG. 4A is a diagram showing an example of a detection signal obtained by a conventional TOC meter.
Figure 4B:
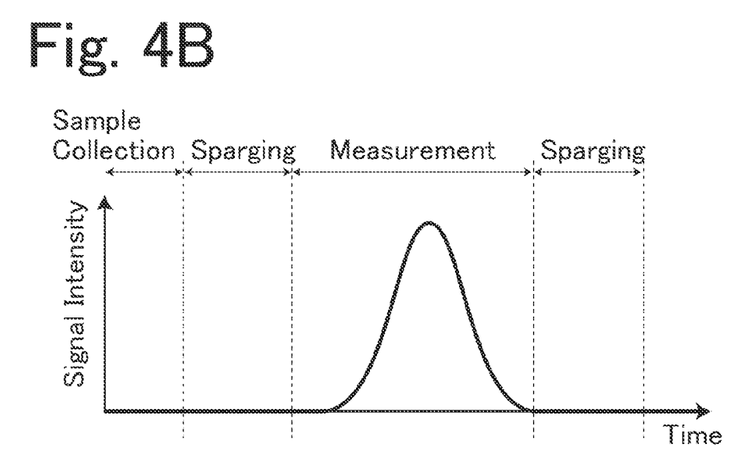
FIG. 4B is a diagram showing an example of a detection signal obtained by a TOC meter of the embodiment.

An example of a waveform of a detection signal obtained by a conventional TOC meter and an example of a waveform of a detection signal obtained by the TOC meter of the above embodiment are schematically shown in FIGS. 4A and 4B, respectively.

As shown in FIG. 4A, conventionally, at the time of sparging inside the syringe pump 4, the flow rate of the carrier gas introduced into the sample cell 44 decreases, and thus, the baseline of the detection signal rises. If measurement is started thereafter, a peak may appear before the baseline of the detection signal returns to a normal state, and in this case, the start point of the peak may be distorted and detection of the peak start point may become difficult, thereby affecting the calculation of the peak area value. In contrast, if the flow rate of the carrier gas introduced into the sample cell 44 is maintained to be constant at all times as in the above embodiment, a change in the baseline of the detection signal may be suppressed and deformation of the peak shape is prevented as shown in FIG. 4B, and the accuracy of TOC measurement may be increased.

In the above embodiment, the carrier gas flowing through the first supply path 56 and the carrier gas flowing through the second supply path 57 are both introduced into the sample cell 44 in the normal state, but the first supply path 56 may be configured as a dedicated path for supplying a sparge gas to the syringe pump 4. An embodiment of a TOC meter configured in such a manner is shown in FIG. 5.

Figure 5:
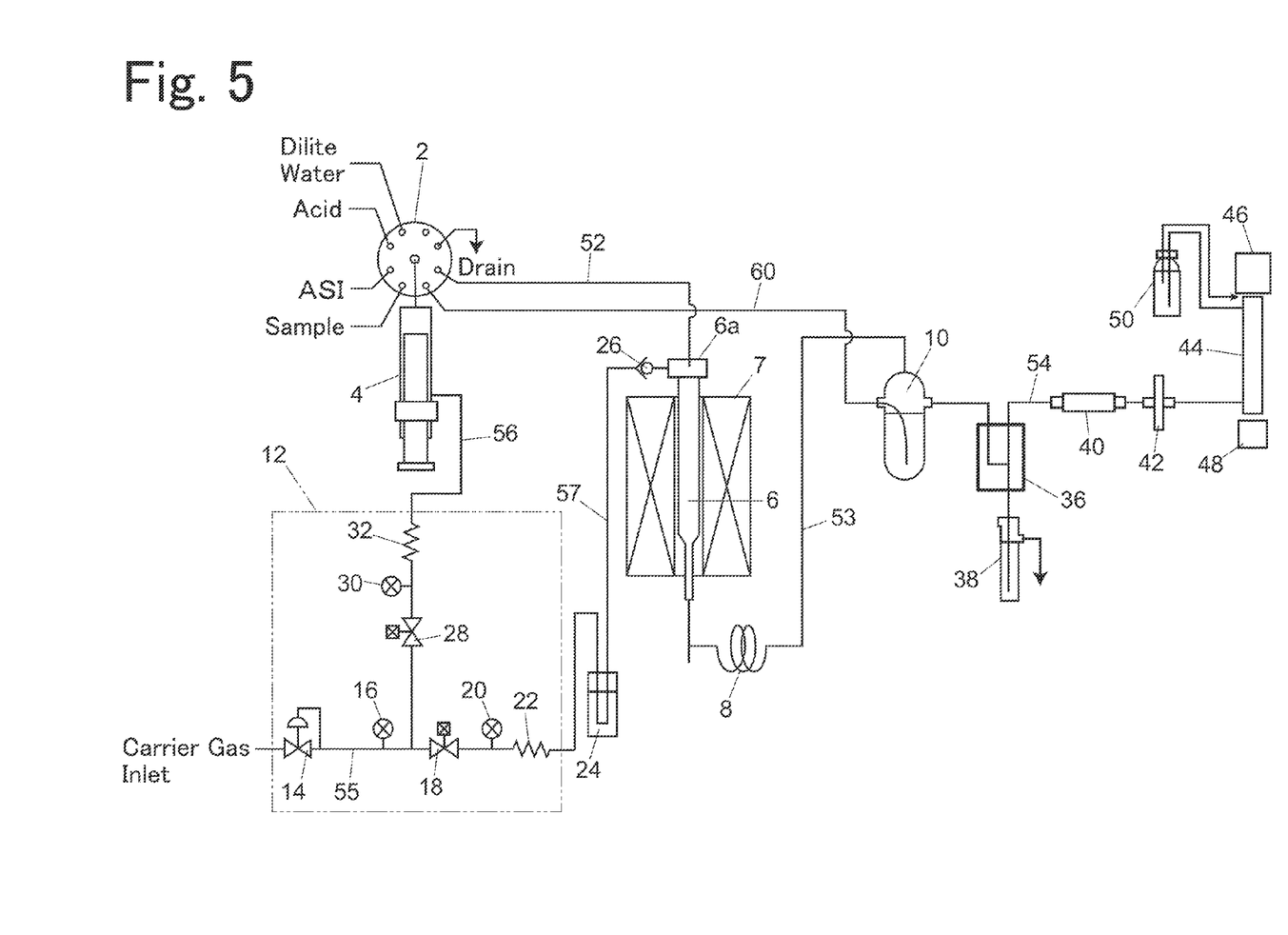
FIG. 5 is a path configuration diagram showing another embodiment of the TOC meter.

In the embodiment in FIG. 5, the first supply path 56 is communicated with the syringe pump 4 at all times. Accordingly, the flow rate control valve 28 is opened to a specific degree of opening only in the sparging state where a carrier gas is supplied to the syringe pump 4 and sparging is performed, and the flow rate control valve 28 is closed in the normal state where sparging is not performed. Since the carrier gas introduced into the sample cell 44 is only the carrier gas flowing through the second supply path 57, the flow rate of the carrier gas introduced into the sample cell 44 may be maintained to be constant simply by maintaining the flow rate control valve 18 at a specific degree of opening.

DESCRIPTION OF REFERENCE SIGNS

2: Multi-port valve
4: Sampling syringe
6: Combustion tube
6a: Sample injection unit
7: Electric furnace
8: Cooling tube
10: Pure water trap
12: Carrier gas supply unit
14: Pressure adjustment valve
16, 20, 30: Pressure sensor
18, 28: Flow rate control valve
22, 32: Flow resistor
34: Electromagnetic valve
34A: Path switching mechanism
36: Dehumidifier
38: Drain port
40: Halogen scrubber
42: Membrane filter
44: Cell
46: Light source
48: Detector
50: $CO_2$ absorber
56: First supply path
57: Second supply path
60: Arithmetic processing unit
62: System controller
64: Valve-opening-degree holding unit
66: Cell flow rate control means

What is claimed is:

1. A total organic carbon measuring device comprising:
a syringe pump for collecting sample water;
an oxidation reaction unit including a combustion tube for oxidatively decomposing and converting, into carbon dioxide carbon components in the sample water collected by the syringe pump, and a heating furnace for heating the combustion tube;
a measurement unit including a sample cell, connected to an outlet portion of the combustion tube, for causing sample gas containing carbon dioxide generated in the combustion tube to flow through, and a detector for measuring carbon dioxide concentration in the sample gas flowing through the sample cell;
a carrier gas supply unit including a carrier gas introduction path for introducing, a carrier vas, a first supply path having one end connected to a downstream end of the carrier gas introduction path and the other end connected in a manner capable of communicating with the syringe pump, a second supply path, different from the first supply path, having one end connected to the downstream end of the carrier gas introduction path and the other end connected to the combustion tube, a first flow rate adjustment mechanism for adjusting a flow rate of the carrier gas flowing through the first supply path, and a second flow rate adjustment mechanism for adjusting, independently from the first flow rate adjustment mechanism, a flow rate of the carrier gas flowing through the second supply path;
a bypass path leading to the sample cell through neither the combustion tube nor the syringe pump for flowing the carrier gas;
a path switching mechanism configured to switch between a sparging state and a normal state, the sparging state communicating the other end of the first supply path with a drain through the syringe pump, and the normal state communicating the other end of the first supply path to the sample cell through the bypass path; and
a system controller configured to control the first flow rate adjustment mechanism and the second flow rate adjustment mechanism in such a way that the carrier gas flows through the first supply path and the second supply path at a predetermined flow rate, the system controller including cell flow rate control means configured to control the first flow rate adjustment mechanism and the second flow rate adjustment mechanism so that a flow rate of the carrier gas introduced into the sample cell through the second supply path in the sparging state and a flow rate of the carrier gas introduced into the sample cell through both the first and second supply paths in the normal state become the same.

2. The total organic carbon measuring device according, to claim 1,
wherein the first flow rate adjustment mechanism and the second flow rate adjustment mechanism adjust the flow rates of carrier gas based on degrees of opening of calves provided on respective paths,
wherein the system controller is configured to control the holding of a first degree of opening that is set in advance as the degree of opening of each valve in the normal state, and a second degree of opening that is set in advance as the degree of opening of each valve in the sparging state, and
wherein the cell flow rate control means is configured to control the setting of each valve of the first flow rate adjustment mechanism and the second flow rate adjustment mechanism at the first degree of opening in the normal state and at the second degree of opening, in the sparging state.

3. The total organic carbon measuring device according to claim 1, wherein the first flow rate adjustment mechanism a flow rate control valve.

4. The total organic carbon measuring device according to claim 1, wherein the second flow rate adjustment mechanism is a flow rate control valve.

5. The total organic carbon measuring device according to claim 1, wherein the path switching mechanism is a three-way electromagnetic valve.

* * * * *